United States Patent
Park et al.

(10) Patent No.: US 11,411,251 B2
(45) Date of Patent: Aug. 9, 2022

(54) ELECTROLYTE, LITHIUM SECONDARY BATTERY INCLUDING THE ELECTROLYTE, AND METHOD OF MANUFACTURING THE ELECTROLYTE

(71) Applicants: Samsung Electronics Co., Ltd., Suwon-si (KR); Samsung SDI Co., Ltd., Yongin-si (KR)

(72) Inventors: Insun Park, Suwon-si (KR); Myongchun Koh, Hwaseong-si (KR); Jinah Seo, Seoul (KR); Dongyoung Kim, Suwon-si (KR); Yeonji Chung, Yongin-si (KR)

(73) Assignees: SAMSUNG ELECTRONICS CO., LTD., Gyeonggi-Do (KR); SAMSUNG SDI CO., LTD., Gyeonggi-Do (KR)

( * ) Notice: Subject to any disclaimer, the term of this patent is extended or adjusted under 35 U.S.C. 154(b) by 242 days.

(21) Appl. No.: 16/707,757

(22) Filed: Dec. 9, 2019

(65) Prior Publication Data
US 2020/0185775 A1    Jun. 11, 2020

(30) Foreign Application Priority Data
Dec. 10, 2018 (KR) .................... 10-2018-0158378

(51) Int. Cl.
| | |
|---|---|
| H01M 6/16 | (2006.01) |
| H01M 10/0567 | (2010.01) |
| C07C 317/02 | (2006.01) |
| C07F 9/141 | (2006.01) |
| H01M 4/36 | (2006.01) |
| H01M 4/505 | (2010.01) |
| H01M 4/525 | (2010.01) |
| H01M 4/62 | (2006.01) |
| H01M 10/0525 | (2010.01) |
| H01M 10/0568 | (2010.01) |
| H01M 10/0569 | (2010.01) |
| H01M 4/02 | (2006.01) |

(52) U.S. Cl.
CPC ....... *H01M 10/0567* (2013.01); *C07C 317/02* (2013.01); *C07F 9/141* (2013.01); *H01M 4/366* (2013.01); *H01M 4/505* (2013.01); *H01M 4/525* (2013.01); *H01M 4/628* (2013.01); *H01M 10/0525* (2013.01); *H01M 10/0568* (2013.01); *H01M 10/0569* (2013.01); *H01M 2004/028* (2013.01)

(58) Field of Classification Search
CPC ......... H01M 10/0567; H01M 10/0569; H01M 10/0568; H01M 10/0566; H01M 10/0525; H01M 10/052; H01M 4/366; H01M 4/362; H01M 4/364; H01M 4/505; H01M 4/525; H01M 4/628; H01M 4/624; H01M 4/621; H01M 2004/028; C07C 317/02; C07C 317/08; C07C 317/04; C07F 9/141; C07F 9/143

See application file for complete search history.

(56) References Cited

U.S. PATENT DOCUMENTS

| | | | |
|---|---|---|---|
| 2009/0191455 A1* | 7/2009 | Gao .................. | H01M 10/4235 252/182.1 |
| 2015/0037668 A1* | 2/2015 | Iwaya ............... | H01M 10/0525 429/200 |
| 2015/0270522 A1* | 9/2015 | Yamada ............. | H01M 50/457 429/145 |
| 2016/0149265 A1* | 5/2016 | Onozaki ........... | H01M 10/0568 429/337 |
| 2018/0053967 A1 | 2/2018 | Koh et al. | |

FOREIGN PATENT DOCUMENTS

| | | |
|---|---|---|
| CN | 101771167 A | 7/2010 |
| CN | 102263292 A | 11/2011 |
| EP | 3355390 A1 | 8/2018 |
| JP | 2001185212 A | 7/2001 |

OTHER PUBLICATIONS

European Search Report for European Patent Application No. 19213517.6 dated Apr. 14, 2020.

* cited by examiner

*Primary Examiner* — Raymond Alejandro
(74) *Attorney, Agent, or Firm* — Cantor Colburn LLP (57) ABSTRACT

An electrolyte including: a lithium salt; a non-aqueous solvent; a compound represented by Formula 1; and a compound represented by Formula 2

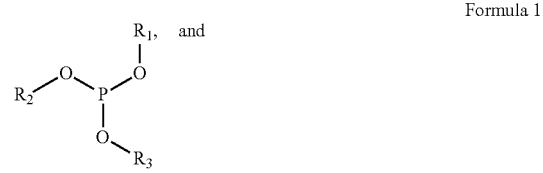

Formula 1

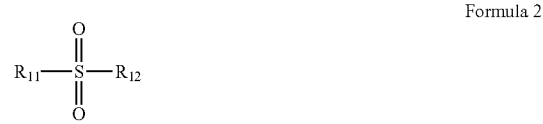

Formula 2 wherein $R_1$, $R_2$, $R_3$, $R_{11}$, and $R_{12}$ in Formulae 1 and 2 are as described in the detailed description.

20 Claims, 1 Drawing Sheet

ELECTROLYTE, LITHIUM SECONDARY BATTERY INCLUDING THE ELECTROLYTE, AND METHOD OF MANUFACTURING THE ELECTROLYTE

CROSS-REFERENCE TO RELATED APPLICATION

This application claims priority to and the benefit of Korean Patent Application No. 10-2018-0158378, filed on Dec. 10, 2018, in the Korean Intellectual Property Office, and all the benefits accruing therefrom under 35 U.S.C. § 119, the content of which is incorporated herein by reference in its entirety.

BACKGROUND

1. Field

The present disclosure relates to an electrolyte including an additive, a lithium secondary battery including the electrolyte, and a method of manufacturing the electrolyte.

2. Description of the Related Art

Lithium secondary batteries are used as power sources for driving portable electronic appliances such as video cameras, mobile phones, and notebook computers. Rechargeable lithium secondary batteries have three times greater specific energy than known lead batteries, nickel-cadmium batteries, nickel metal hydride batteries, and nickel-zinc batteries, and may be charged at a high rate.

A lithium metal oxide is used as a cathode active material in a cathode of a lithium secondary battery. For example, a composite oxide of lithium and a metal such as cobalt (Co), manganese (Mn), and/or nickel (Ni), may be used. Among these, in the case of high-Ni-content cathode active material, it is possible to provide a higher capacity battery as compared with a lithium cobalt oxide.

However, in the case of a high-Ni-content cathode active material, since the surface structure of a cathode is weak, lifetime characteristics are poor, and a large amount of gas is generated.

Therefore, there is a need to develop a lithium secondary battery including a high-Ni-content cathode active material, which exhibits high capacity, good lifetime characteristics, and improved gas production characteristics.

SUMMARY

Provided is an electrolyte and a method of manufacturing the electrolyte.

Provided is a lithium secondary battery including the electrolyte.

Additional aspects will be set forth in part in the description which follows and, in part, will be apparent from the description, or may be learned by practice of the presented embodiment.

According to an aspect of an embodiment, an electrolyte includes: a lithium salt; a non-aqueous solvent; a compound represented by Formula 1; and a compound represented by Formula 2

Formula 1

Formula 2 wherein, in Formulas 1 and 2, $R_1$ to $R_3$ are each independently a substituted or unsubstituted $C_1$-$C_{30}$ alkyl group, a substituted or unsubstituted $C_6$-$C_{60}$ aryl group, or a substituted or unsubstituted $C_1$-$C_{60}$ heteroaryl group, and $R_{11}$ and $R_{12}$ are each independently hydrogen, deuterium, a hydroxyl group, a vinyl group, an allyl group, a substituted or unsubstituted $C_1$-$C_{30}$ alkyl group, a substituted or unsubstituted $C_2$-$C_{10}$ alkenyl group, a substituted or unsubstituted $C_2$-$C_{10}$ alkynyl group, a substituted or unsubstituted $C_6$-$C_{60}$ aryl group, or a substituted or unsubstituted $C_1$-$C_{60}$ heteroaryl group.

According to an aspect of an embodiment, a lithium secondary battery includes: a cathode; an anode; and the electrolyte disposed between the cathode and the anode, wherein the cathode includes a cathode active material represented by Formula 3,

$$Li_xNi_yM_{1-y}O_{2-z}A_z.\qquad\text{Formula 3}$$

wherein, in Formula 3, $0.9 \le x \le 1.2$, $0.1 \le y \le 0.98$, and $0 \le z < 0.2$, M is Al, Mg, Mn, Co, Fe, Cr, V, Ti, Cu, B, Ca, Zn, Zr, Nb, Mo, Sr, Sb, W, or Bi; and A is an element having an oxidation number of −1, −2, or −3.

Also disclosed a method of manufacturing an electrolyte, the method including: contacting a lithium salt, a non-aqueous solvent, a compound represented by Formula 1, and a compound represented by Formula 2 to manufacture the electrolyte Formula 1

Formula 2 wherein, in Formulas 1 and 2, $R_1$ to $R_3$ are each independently a substituted or unsubstituted $C_1$-$C_{30}$ alkyl group, a substituted or unsubstituted $C_6$-$C_{60}$ aryl group, or a substituted or unsubstituted $C_1$-$C_{60}$ heteroaryl group, and $R_{11}$ and $R_{12}$ are each independently hydrogen, deuterium, a hydroxyl group, a vinyl group, an allyl group, a substituted or unsubstituted $C_1$-$C_{30}$ alkyl group, a substituted or unsubstituted $C_2$-$C_{10}$ alkenyl group, a substituted or unsubstituted $C_2$-$C_{10}$ alkynyl group, a substituted or unsubstituted $C_6$-$C_{60}$ aryl group, or a substituted or unsubstituted $C_1$-$C_{60}$ heteroaryl group.

BRIEF DESCRIPTION OF THE DRAWINGS

These and/or other aspects will become apparent and more readily appreciated from the following description of the embodiments, taken in conjunction with a FIG. 1 which is a schematic view of a lithium secondary battery according to an example embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the FIGURES, to explain aspects. As used herein, the term "and/or" includes any and all combinations of one or more of the associated listed items. "Or" means "and/or." Expressions such as "at least one of," when preceding a list of elements, modify the entire list of elements and do not modify the individual elements of the list.

It will be understood that when an element is referred to as being "on" another element, it can be directly on the other element or intervening elements may be present therebetween. In contrast, when an element is referred to as being "directly on" another element, there are no intervening elements present.

It will be understood that, although the terms "first," "second," "third," etc. may be used herein to describe various elements, components, regions, layers, and/or sections, these elements, components, regions, layers, and/or sections should not be limited by these terms. These terms are only used to distinguish one element, component, region, layer or section from another element, component, region, layer, or section. Thus, "a first element," "component," "region," "layer," or "section" discussed below could be termed a second element, component, region, layer, or section without departing from the teachings herein.

The terminology used herein is for the purpose of describing particular embodiments only and is not intended to be limiting. As used herein, "a," "an," "the," and "at least one" are do not denote a limitation of quantity, and are intended to cover both the singular and plural, unless the context clearly indicates otherwise. For example, "an element" has the same meaning as "at least one element," unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the FIGURES. It will be understood that relative terms are intended to encompass different orientations of the device in addition to the orientation depicted in the FIGURES. For example, if the device in one of the FIGURES is turned over, elements described as being on the "lower" side of other elements would then be oriented on "upper" sides of the other elements. The exemplary term "lower," can therefore, encompasses both an orientation of "lower" and "upper," depending on the particular orientation of the FIGURE. Similarly, if the device in one of the FIGURES is turned over, elements described as "below" or "beneath" other elements would then be oriented "above" the other elements. The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10% or 5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

"Alkyl" as used herein means a straight or branched chain saturated aliphatic monovalent hydrocarbon group having the specified number of carbon atoms, specifically 1 to 12 carbon atoms, more specifically 1 to 6 carbon atoms. Alkyl groups include, for example, groups having from 1 to 50 carbon atoms ($C_1$ to $C_{50}$ alkyl).

"Alkenyl" means a straight or branched chain, aliphatic monovalent hydrocarbon group having at least one carbon-carbon double bond (e.g., ethenyl (—HC=$CH_2$)).

"Alkynyl" means a straight or branched chain, aliphatic monovalent hydrocarbon group having at least one carbon-carbon triple bond (e.g., ethynyl).

"Aryl" means a monovalent group formed by the removal of one hydrogen atom from one or more rings of an arene (e.g., phenyl or naphthyl).

"Alkoxy" means an alkyl group that is linked via an oxygen (i.e., —O-alkyl). Non-limiting examples of $C_1$ to $C_{30}$ alkoxy groups include methoxy groups, ethoxy groups, propoxy groups, isobutyloxy groups, sec-butyloxy groups, pentyloxy groups, iso-amyloxy groups, and hexyloxy groups.

The prefix "hetero" means that the compound or group includes at least one a heteroatom (e.g., 1, 2, or 3 heteroatom(s)), wherein the heteroatom(s) is each independently N, O, S, Si, or P.

"Heteroaryl" means a monovalent cyclic ring group that includes one or more aromatic rings, in which at least one ring member (e.g., one, two or three ring members) is a heteroatom. In a $C_3$ to $C_{30}$ heteroaryl, the total number of ring carbon atoms ranges from 3 to 30, with remaining ring atoms being heteroatoms. Multiple rings, if present, may be pendent, spiro or fused. The heteroatom(s) are independently at least one of nitrogen (N), oxygen (O), P (phosphorus), or sulfur (S).

"Substituted" means that the compound or group is substituted with a (e.g., 1, 2, 3, or 4) substituent(s), and the substituents are independently a hydroxyl (—OH), a C1-9 alkoxy, a C1-9 haloalkoxy, an oxo (=O), a nitro (—$NO_2$), a cyano (—CN), an amino (—NH$_2$), an azido (—N$_3$), an amidino (—C(=NH)NH$_2$), a hydrazino (—NHNH$_2$), a hydrazono (=N—NH$_2$), a carbonyl (—C(=O)—), a carbamoyl group (—C(O)NH$_2$), a sulfonyl (—S(=O)$_2$—), a thiol group (—SH), a thiocyano (—SCN), a tosyl (CH$_3$C$_6$H$_4$SO$_2$—), a carboxylic acid group (—C(=O)OH), a carboxylic C1 to C6 alkyl ester group (—C(=O)OR wherein R is a C1 to C6 alkyl group), a carboxylic acid salt group (—C(=O)OM) wherein M is an organic or inorganic cation, a sulfonic acid group (—SO$_3$H$_2$), a sulfonic mono- or dibasic salt group (—SO$_3$MH or —SO$_3$M$_2$ wherein M is an organic or inorganic cation), a phosphoric acid group (—PO$_3$H$_2$), a phosphoric acid mono- or dibasic salt group (—PO$_3$MH or —PO$_3$M$_2$ wherein M is an organic or inorganic cation), a C1 to C12 alkyl, a C3 to C12 cycloalkyl, a C2 to C12 alkenyl, a C5 to C12 cycloalkenyl, a C2 to C12 alkynyl, a C6 to C12 aryl, a C7 to C13 arylalkyl, a C4 to C12 heterocycloalkyl, or a C3 to C12 heteroaryl instead of hydrogen, provided that the substituted atom's normal valence is not exceeded. The indicated number of carbon atoms for any group herein is exclusive of any substituents.

The C rate is a discharge rate of a cell, and is obtained by dividing a total capacity of the cell by a total discharge period of time of 1 hour, e.g., a C rate for a battery having a discharge capacity of 1.6 ampere-hours would be 1.6 amperes.

Hereinafter, an electrolyte, and a lithium secondary battery according to example embodiments will be described in further detail.

An electrolyte according to an embodiment comprises: a lithium salt; a non-aqueous solvent; a compound represented by Formula 1; and a compound represented by Formula 2

Formula 1

Formula 2

In the compounds of Formulae 1 and 2, $R_1$ to $R_3$ are each independently a substituted or unsubstituted $C_1$-$C_{30}$ alkyl group, a substituted or unsubstituted $C_6$-$C_{60}$ aryl group, or a substituted or unsubstituted $C_1$-$C_{60}$ heteroaryl group; and $R_{11}$ and $R_{12}$ are each independently hydrogen, deuterium, a hydroxyl group, a vinyl group, an allyl group, a substituted or unsubstituted $C_1$-$C_{30}$ alkyl group, a substituted or unsubstituted $C_2$-$C_{10}$ alkenyl group, a substituted or unsubstituted $C_2$-$C_{10}$ alkynyl group, a substituted or unsubstituted $C_6$-$C_{60}$ aryl group, or a substituted or unsubstituted $C_1$-$C_{60}$ heteroaryl group.

As will be further described later, when a lithium metal composite oxide having a high-Ni-content is used as a cathode active material, in spite of providing improved capacity, deterioration of lifetime characteristics, such as capacity retention and resistance increase, is serious, and a large amount of gas is generated at high temperature, so that it is difficult to commercialize.

First, and while not wanting to be bound by theory, it is understood that the deterioration of lifetime characteristics, such as a capacity retention and a resistance increase, is primarily caused by a disproportionation reaction in which $Ni^{3+}$ cations are eluted from a cathode into an electrolyte, or the $Ni^{3+}$ cation is converted into a $Ni^{4+}$ cation during a battery discharge to produce NiO. Thus, lifetime characteristics deteriorate, and resistance increases. Therefore, in order to overcome these problems, when the electrolyte includes the phosphite-based compound represented by Formula 1, a $Ni^{3+}$ cation is protected, thereby preventing the elution of $Ni^{3+}$ cation and the disproportionation reaction.

Further, the generation of gas at elevated temperature is understood to be primarily caused by decomposing an SEI film using a $Ni^{3+}$ cation eluted from a cathode. Therefore, in order to overcome this problem, the electrolyte includes the sulfone-based compound represented by Formula 2, and a sulfone-containing protective film is formed on the surface of an anode, thereby preventing the decomposition of the SEI film to suppress the generation of gas at hot temperature. As a result, the electrolyte may suppress the generation of gas at elevated temperature of a lithium secondary battery, and may improve the performance of a lithium secondary battery.

In this case, a phosphite-based compound of Formula 1 may be included in the electrolyte in an amount of about 0.1 weight percent (wt %) to about 5 wt %, about 0.2 wt % to about 4 wt %, about 0.5 wt % to about 3 wt %, or about 0.7 wt % to 1.5 wt % based on the total weight of the electrolyte. However, the amount of the compound of Formula 1 is not limited thereto, and may be contained in any suitable amount in which $Ni^{3+}$ eluted from the cathode active material into the electrolyte is stabilized. When the amount of the compound of Formula 1 is more than about 5 wt %, the self-decomposition of the phosphite-based compound may occur, resulting in increased film resistance, and the produced $CO_2$ adversely affects the electrolyte, so that battery capacity, storage stability, and cycle characteristics may be deteriorated. When the amount of the compound of Formula 1 is less than about 0.1 wt %, the amount thereof may be too small to sufficiently stabilize $Ni^{3+}$, and thus a sufficient resistance decrease effect is difficult to obtain.

For example, the compound of Formula 1 may be included in an amount of about 0.1 wt % to about 3 wt %, based on the total weight of the electrolyte. For example, the compound of Formula 1 may be included in an amount of about 0.2 wt % to about 3 wt %, based on the total weight of the electrolyte.

Further, the compound of Formula 2 may be included in the electrolyte in an amount of about 0.1 wt % to about 3 wt %, based on the total weight of the electrolyte. However, the amount of the compound of Formula 2 is not limited thereto, and may be available in any suitable amount in which a protective film is easily formed on the surface of an anode. When the amount of the compound of Formula 2 is more than about 3 wt %, the self-decomposition of the sulfone-based compound may occur, resulting in increased film resistance, and the produced $CO_2$ adversely affects the electrolyte, so that battery capacity, storage stability, and cycle characteristics may be deteriorated. When the amount of the compound of Formula 2 is less than about 0.1 wt %, the amount thereof may be too little to sufficiently form the protective film, and a sufficient resistance decrease effect is difficult to obtain.

For example, the compound of Formula 2 may be included in an amount of about 0.1 wt % to about 2 wt %, based on the total weight of the electrolyte. For example, the compound of Formula 2 may be included in an amount of about 0.3 wt % to about 1 wt %, based on the total weight of the electrolyte.

In Formulas 1 and 2, $R_1$ to $R_3$ are each independently a substituted or unsubstituted $C_1$-$C_{30}$ alkyl group, a substituted or unsubstituted $C_6$-$C_{60}$ aryl group, or a substituted or unsubstituted $C_1$-$C_{60}$ heteroaryl group.

The $C_1$-$C_{30}$ alkyl group may be, for example, a methyl group, an ethyl group, a propyl group, an isopropyl group, a butyl group, a sec-butyl group, a tert-butyl group, or an isobutyl group, but is not limited thereto.

The $C_6$-$C_{60}$ aryl group may be, for example, a phenyl group, a biphenyl group, or a terphenyl group, but is not limited thereto.

The $C_1$-$C_{60}$ heteroaryl group may be, for example, a pyridinyl group, a pyrimidinyl group, a pyridazinyl group, a pyrazinyl group, a triazinyl group, a pyrrolyl group, an imidazolyl group, a pyrazolyl group, an oxazolyl group, a thiazolyl group, or a triazolyl group, but is not limited thereto.

For example, in Formulas 1 and 2, $R_1$ to $R_3$ may be each independently a methyl group, an ethyl group, a propyl group, an isopropyl group, a butyl group, a sec-butyl group, a tert-butyl group, an isobutyl group, or a phenyl group; or a methyl group, an ethyl group, a propyl group, an isopropyl group, a butyl group, a sec-butyl group, a tert-butyl group, or an isobutyl group, each being optionally substituted with at least one of deuterium ($^2$H or D), —F, —Cl, —Br, —I, a cyano group, a nitro group, a hydroxyl group, a methyl group, an ethyl group, or a propyl group.

For example, the compound of Formula 1 may be at least one of trimethyl phosphite, triethyl phosphite, tributyl phosphite, triphenyl phosphite, tri-o-tolyl phosphite, tri(2-furyl) phosphite, or diethyl phenyl phosphite.

tri-o-tolyl phosphite      tri(2-furyl) phosphite

In Formulas 1 and 2, $R_{11}$ and $R_{12}$ are each independently hydrogen, deuterium, a hydroxyl group, a vinyl group, an allyl group, a substituted or unsubstituted $C_1$-$C_{30}$ alkyl group, a substituted or unsubstituted $C_2$-$C_{10}$ alkenyl group, a substituted or unsubstituted $C_2$-$C_{10}$ alkynyl group, a substituted or unsubstituted $C_6$-$C_{60}$ aryl group, or a substituted or unsubstituted heteroaryl group.

For example, $R_{11}$ and $R_{12}$ may each independently be a vinyl group or an allyl group. That is, the compound of Formula 2 may include at least one double bond.

For example, the compound of Formula 2 may be divinyl sulfone, allyl phenyl sulfone, allyl methyl sulfone, or phenyl vinyl sulfone.

For example, the compound of Formula 2 may be compound 101, 102, 103, 104, or 105:

101

102

103

104

105

The electrolyte includes a lithium salt. The lithium salt is dissolved in an organic solvent, and may act as a source of lithium ions in the battery. For example, the lithium salt may promote the movement of lithium ions between the cathode and the anode.

The anion of the lithium salt included in the electrolyte may be at least one of $PF_6^-$, $BF_4^-$, $SbF_6^-$, $AsF_6^-$, $C_4F_9SO_3^-$, $ClO_4^-$, $AlO_2^-$, $AlCl_4^-$, $C_xF_{2x+1}SO_3^-$ (here, x is a natural number), $(C_xF_{2x+1}SO_2)(C_yF_{2y+1}SO_2)N^-$ (here, x and y are natural numbers), or a halide.

For example, the lithium salt may be at least one of lithium difluoro (oxalate)borate (LiDFOB), lithium bis(oxalato)borate (LiBOB), lithium difluoro bis(oxalato) phosphate (LiDFOP), lithium difluorophosphate (LiPO$_2$F$_2$), LiBF$_4$, LiPF$_6$, LiCF$_3$SO$_3$, LiN(CF$_3$SO$_2$)$_2$, or LiN(FSO$_2$)$_2$. For example, the lithium salt may be LiPF$_6$, LiBOB, or LiPO$_2$F$_2$.

LiDFOB

A plurality of the aforementioned lithium salts may be used. For example, the electrolyte may include LiPF$_6$ having a concentration of about 0.6 M to about 2.0 M as a primary salt, and may include another salt, such as LiDFOB, LiBOB, LiDFOP, LiPO$_2$F$_2$, LiBF$_4$, LiCF$_3$SO$_3$, LiN(CF$_3$SO$_2$)$_2$, or LiN(FSO$_2$)$_2$ in an amount not exceeding the amount of the primary salt.

In detail, the electrolyte may include LiPF$_6$ having a concentration of about 1 M to about 1.5 M as a primary salt, and may include LiBOB, LiPO$_2$F$_2$, and the like in an amount of about 0.5 wt % to about 10 wt %, about 1 wt % to about 8 wt %, or about 1.5 wt % to about 6 wt %, based on the total weight of the electrolyte.

The non-aqueous solvent may be an aprotic solvent, and may be at least one of a carbonate-based solvent, an ester-based solvent, an ether-based solvent, or a ketone-based solvent. As the carbonate-based solvent, at least one of dimethyl carbonate (DMC), diethyl carbonate (DEC), ethyl methyl carbonate (EMC), dipropyl carbonate (DPC), methyl propyl carbonate (MPC), ethyl propyl carbonate (EPC), ethylene carbonate (EC), propylene carbonate (PC), or butylene carbonate (BC) may be used. As the ester-based solvent, at least one of methyl acetate, ethyl acetate, n-propyl acetate, t-butyl acetate, methyl propionate, ethyl propionate, γ-butyrolactone, decanolide, valerolactone, mevalonolactone, or caprolactone may be used. As the ether-based solvent, at least one of dibutyl ether, tetraglyme, diglyme, dimethoxyethane, 2-methyltetrahydrofuran, or tetrahydrofuran may be used. As the ketone-based solvent, cyclohexanone may be used. The aprotic solvent may be used alone, or may be used as a mixture of two or more solvents. When a mixture of two or more solvents is used as the organic solvent, the mixing ratio thereof may be appropriately selected depending on battery performance.

The non-aqueous solvent may be used alone, or may be used as a mixture of two or more. When a mixture of two or more is used as the organic solvent, the content of each solvent may be appropriately selected depending on battery performance.

In the case of the carbonate-based solvent, a mixture of a linear carbonate and a cyclic carbonate may be used. In this case, when the linear carbonate and the cyclic carbonate are mixed at a volume ratio of about 1:1 to about 9:1, about 2:1 to about 9:1, or about 3:1 to about 9:1, the performance of the electrolyte may be improved relative to a composition in which a volume ratio of the linear carbonate and the cyclic carbonate are not about 1:1 to about 9:1.

In an aspect, the non-aqueous solvent may further include at least one of fluoroethylene carbonate (FEC), vinylene carbonate (VC), vinylethylene carbonate (VEC), a phosphorus (P)-containing compound, or a sulfur (S)-containing compound.

The non-aqueous solvent may further include fluoroethylene carbonate (FEC). For example, the non-aqueous solvent may further include FEC in an amount of about 0.1 volume percent (vol %) to about 20 vol %, based on the total volume of the non-aqueous solvent. For example, the non-aqueous solvent may further include FEC in an amount of about 0.5 vol % to about 20 vol % based on the total volume of the non-aqueous solvent. For example, the non-aqueous solvent may further include FEC in an amount of about 1 vol % to about 15 vol % based on the total volume of the non-aqueous solvent. When FEC is included in the non-aqueous solvent in the above amount, an effective SEI film not inhibiting the diffusion of lithium ions may be rapidly formed.

The electrolyte may include at least one of a carbonate having a carbon-carbon single bond or a carbon-carbon multiple bond, or a carboxylic anhydride having a carbon-carbon single bond or a carbon-carbon multiple bond. The multiple bond may be a double bond or a triple bond, and the carbonate or carboxylic anhydride may be linear or cyclic.

The electrolyte may further include at least one of vinylene carbonate (VC), vinylethylene carbonate (VEC), maleic anhydride, succinic anhydride, or succinonitrile (SN). For example, the electrolyte may further include SN.

For example, the electrolyte may further include at least one of VC, VEC, maleic anhydride, succinic anhydride, or SN. A content may be in an amount of about 0.1 wt % to about 2 wt %, based on the total weight of the electrolyte.

For example, the electrolyte may further include at least one of VC, VEC, maleic anhydride, succinic anhydride, or SN in an amount of about 0.1 wt % to about 1.5 wt %, based on the total weight of the electrolyte.

In an embodiment, the electrolyte may further include SN, and the amount of SN is not limited thereto. For example, the electrolyte may comprise SN in an amount of about 0.1 wt % to about 1.5 wt %, based on the total weight of the electrolyte. For example, the electrolyte may comprise SN in an amount of about 0.1 wt % to about 1.0 wt %, based on the total weight of the electrolyte. For example, the electrolyte may comprise SN in an amount of about 0.1 wt % to about 0.5 wt % based on the total weight of the electrolyte.

While not wanting to be bound by theory, it is understood that the compound of Formula 1 or compound of Formula 2 is easily decomposed by a reaction with an anode, and, as will be further described later, the lifetime characteristics of a lithium secondary battery including an anode active material including a metal alloyable with lithium or a carbon-based anode active material are deteriorated due to gas generation caused by catalysis at high temperature. As described above, when the lithium salt, FEC, SN, or the like is included within the above range, a passivation film including the chemical reaction products of the above materials, that is, an SEI film, may be formed on a portion of the surface of an anode, or on an entire surface of the anode. Since the generation of gas during high-temperature storage may be prevented by the SEI film, improvement in stability and performance of the lithium secondary battery may be realized.

Another aspect of the present disclosure provides a lithium secondary battery. The lithium secondary battery includes: a cathode; an anode; and the electrolyte disposed between the cathode and the anode, wherein the cathode includes a cathode active material represented by Formula 3:

$$Li_xNi_yM_{1-y}O_{2-z}A_z$$  Formula 3

In Formula 3, $0.9 \leq x \leq 1.2$, $0.1 \leq y \leq 0.98$, and $0 \leq z < 0.2$ are satisfied; M is at least one of Al, Mg, Mn, Co, Fe, Cr, V, Ti, Cu, B, Ca, Zn, Zr, Nb, Mo, Sr, Sb, W, or Bi; and A is an element having an oxidation number of −1, −2, or −3.

For example, in Formula 3, A may be a halogen, S, or N, but is not limited thereto.

For example, in Formula 3, y, which represents the amount of Ni in the cathode active material, may be $0.3 \leq y \leq 0.98$ satisfied.

For example, $0.7 \leq y \leq 0.98$ in Formula 3 may be satisfied. For example, $0.8 \leq y \leq 0.95$ in Formula 3 may be satisfied. For example, $0.88 \leq y \leq 0.94$ in Formula 3 may be satisfied. When the amount of Ni in the cathode active material is less than 70%, since the amount thereof is too small, although the deterioration of the lifetime characteristics of the high-Ni-content cathode active material, such as $Ni^{3+}$ cation elution or disproportionation, is insignificant due to a stable surface structure, lifetime decreases and resistance characteristics are poor. The reduced lifetime and increased resistance is understood to be due to a mechanism in which phosphite, having an affinity with $Ni^{3+}$, is located on a surface and thus resistance increases.

For example, the cathode active material may be represented by Formulas 4 or 5.

$$Li_{x'}Ni_{y'}Co_{1-y'-z'}Al_{z'}O_2$$  Formula 4

$$Li_{x'}Ni_{y'}Co_{1-y'-z'}Mn_{z'}O_2$$  Formula 5

In Formulas 4 and 5, x', y', and z' are each independently $0.9 \leq x' \leq 1.2$, $0.8 \leq y' \leq 0.98$, $0 < z' < 0.1$, and $0 < 1-y'-z' < 0.2$.

For example, the cathode may include at least one of LiNi$_{0.88}$Co$_{0.08}$Mn$_{0.04}$O$_2$, LiNi$_{0.88}$Co$_{0.08}$Al$_{0.04}$O$_2$, LiNi$_{0.91}$Co$_{0.06}$Mn$_{0.03}$O$_2$, LiNi$_{0.91}$Co$_{0.06}$Al$_{0.03}$O$_2$, Li$_{1.02}$Ni$_{0.88}$Co$_{0.08}$Mn$_{0.04}$O$_2$, Li$_{1.02}$Ni$_{0.88}$Co$_{0.08}$Al$_{0.04}$O$_2$, Li$_{1.02}$Ni$_{0.91}$Co$_{0.06}$Mn$_{0.03}$O$_2$, or Li$_{1.02}$Ni$_{0.91}$Co$_{0.06}$Al$_{0.03}$O$_2$ as the cathode active material. However, the present disclosure is not limited thereto.

As described above, in the case of a lithium metal composite oxide having a high-Ni-content, in spite of providing high-capacity, as the amount of Ni$^{3+}$ cations increases, lifetime characteristics are poor, resistance is high, and the generation amount of gas increases at a high temperature. Accordingly, when the electrolyte includes the phosphite-based compound represented by Formula 1, Ni$^{3+}$ cations are protected, thereby preventing the elution of Ni$^{3+}$ cations and the disproportionation reaction. Further, in order to prevent the generation of gas at a high temperature, e.g., about 20° C. to about 100° C., about 30° C. to about 90° C., or about 40° C. to about 80° C., which is understood to be caused by decomposing an SEI film on the surface of the anode using the Ni$^{3+}$ cations eluted from the cathode, the electrolyte includes the sulfone-based compound represented by Formula 2, thereby forming a protective film containing sulfone on the surface of the anode, so that the decomposition of the SEI film is suppressed, and thus the generation of gas at high temperature is suppressed.

The cathode may further include at least one of lithium cobalt oxide, lithium nickel cobalt manganese oxide, lithium nickel cobalt aluminum oxide, lithium iron phosphorus oxide, or lithium manganese oxide, in addition to the aforementioned cathode active material. However, the present disclosure is not limited thereto, and the cathode may further include any suitable cathode active material available in the art.

For example, the cathode active material may further include a compound represented by at least one of: Li$_a$A$_{1-b}$J$_b$D'$_2$ (here, 0.90≤a≤1.8 and 0≤b≤0.5 are satisfied); Li$_a$E$_{1-b}$J$_b$O$_{2-c}$D'$_c$ (here, 0.90≤a≤1.8, 0≤b≤0.5, and 0≤c≤0.05 are satisfied); LiE$_{2-b}$J$_b$O$_{4-c}$D'$_c$ (here, 0≤b≤0.5 and 0≤c≤0.05 are satisfied); Li$_a$Ni$_{1-b-c}$Co$_b$J$_c$D$_\alpha$ (here, 0.90≤a≤1.8, 0≤b≤0.5, 0≤c≤0.05, and 0<α≤2 are satisfied); Li$_a$Ni$_{1-b-c}$Co$_b$J$_c$O$_{2-\alpha}$F'$_\alpha$ (here, 0.90≤a≤1.8, 0≤b≤0.5, 0≤c≤0.05, and 0<α≤2 are satisfied); Li$_a$Ni$_{1-b-c}$Co$_b$J$_c$O$_{2-\alpha}$F'$_2$ (here, 0.90≤a≤1.8, 0≤b≤0.5, 0≤c≤0.05, and 0<α<2 are satisfied); Li$_a$Ni$_{1-b-c}$Mn$_b$J$_c$D$_\alpha$ (here, 0.90≤a≤1.8, 0≤b≤0.5, 0≤c≤0.05, and 0<α<2 are satisfied); Li$_a$Ni$_{1-b-c}$Mn$_b$J$_c$O$_{2-\alpha}$F'$_\alpha$ (here, 0.90≤a≤1.8, 0≤b≤0.5, 0≤c≤0.05, and 0<α<2 are satisfied); Li$_a$Ni$_{1-b-c}$Mn$_b$J$_c$O$_{2-\alpha}$F'$_2$ (here, 0.90≤a≤1.8, 0≤b≤0.5, 0≤c≤0.05, and 0<α<2 are satisfied); Li$_a$Ni$_b$E$_c$G$_d$O$_2$ (here, 0.90≤a≤1.8, 0≤b≤0.9, 0≤c≤0.5, and 0.001≤d≤0.1 are satisfied); Li$_a$Ni$_b$Co$_c$Mn$_d$G$_e$O$_2$ (here, 0.90≤a≤1.8, 0≤b≤0.9, 0≤c≤0.5, 0≤d≤0.5, and 0.001≤e≤0.1 are satisfied); Li$_a$NiG$_b$O$_2$ (here, 0.90≤a≤1.8 and 0.001≤b≤0.1 are satisfied); Li$_a$CoG$_b$O$_2$ (here, 0.90≤a≤1.8 and 0.001≤b≤0.1 are satisfied); Li$_a$MnG$_b$O$_2$ (here, 0.90≤a≤1.8 and 0.001≤b≤0.1 are satisfied); Li$_a$Mn$_2$G$_b$O$_4$ (here, 0.90≤a≤1.8 and 0.001≤b≤0.1 are satisfied); QO$_2$; QS$_2$; LiQS$_2$; V$_2$O$_5$; LiV$_2$O$_5$; LiRO$_2$; LiNiVO$_4$; Li$_{(3-f)}$T$_2$(PO$_4$)$_3$ (0≤f≤2); Li$_{(3-f)}$Fe$_2$(PO$_4$)$_3$ (0≤f≤2); or LiFePO$_4$.

In the formulae above, A is at least one of Ni, Co, or Mn; J is at least one of Al, Ni, Co, Mn, Cr, Fe, Mg, Sr, V, or a rare earth element; D' is at least one of O, F, S, or P; E is at least one of Co or Mn; F' is at least one of F, S, or P; G is at least one of Al, Cr, Mn, Fe, Mg, La, Ce, Sr, or V; Q is at least one of Ti, Mo, or Mn; R is at least one of Cr, V, Fe, Sc, or Y; and T is at least one of V, Cr, Mn, Co, Ni, or Cu.

First, a cathode is prepared by the following method.

The cathode may be prepared by applying, drying, and pressing a cathode active material composition on a cathode current collector. In addition to the above-described cathode active materials, a cathode active material composition in which a binder and a solvent are mixed may be prepared, if desired.

The cathode active material composition may further include a conductive agent or a filler.

In an embodiment, the cathode active material composition may directly be coated on a metallic current collector and then dried to prepare a cathode plate. In an embodiment, the cathode active material composition may be cast on a separate support to form a cathode active material film, which may then be separated from the support and laminated on a metallic current collector to prepare a cathode plate.

In an embodiment, a loading level of a prepared cathode active material composition may be about 30 milligrams per square centimeter (mg/cm$^2$) or greater, and in an embodiment, about 35 mg/cm$^2$ or greater, and in an embodiment, about 40 mg/cm$^2$ or greater, e.g., about 30 mg/cm$^2$ to about 200 mg/cm$^2$, or about 40 mg/cm$^2$ to about 150 mg/cm$^2$. In addition, an electrode density of the cathode may be about 3 grams per cubic centimeter (g/cc) or greater, and in some embodiments, about 3.5 g/cc or greater, or about 3 g/cc to about 10 g/cc.

In an embodiment, for high cell energy density, the loading level of the prepared cathode active material composition may be about 35 mg/cm$^2$ to about 50 mg/cm$^2$, and the electrode density may be about 3.5 g/cc to about 7.5 g/cc, or more.

In an embodiment, both sides of the cathode current collector may be coated with the cathode active material composition at a loading level of 37 mg/cm$^2$ and an electrode density of 3.6 g/cc.

When the loading level of the cathode active material composition and the electrode density satisfy the above ranges, a battery including this cathode active material may exhibit a high cell energy density of 500 Watt-hour per liter (Wh/L) or more. For example, the battery may exhibit a cell energy density of about 500 Wh/L to about 900 Wh/L.

For example, the cathode may have a Brunauer-Emmett-Teller (BET) specific surface area of about 8 square meters per gram (m$^2$/g) to about 10 m$^2$/g, and a tap density of 3 grams per cubic centimeter (g/cm$^3$) or more. For example, the tap density of the cathode may be about 3 g/cm$^3$ to about 10 g/cm$^3$, but is not limited thereto.

As the solvent, at least one of N-methylpyrrolidone, acetone, or water may be used. The amount of the solvent may be about 10 parts by weight to about 100 parts by weight, based on 100 parts by weight of the cathode active material. When the amount of the solvent is within the above range, it is easy to form an active material layer.

The conductive agent is added in an amount of about 1 wt % to about 30 wt %, based on the total weight of the mixture including the cathode active material. This conductive agent is not limited as long as it has suitable electrical conductivity without causing an undesirable chemical change in the battery, and examples thereof may include graphite such as natural graphite or artificial graphite; carbon black, acetylene black, ketjen black, channel black, furnace black, lamp black, or summer black; a conductive fiber such as carbon fiber or a metal fiber; carbon fluoride; a metal powder such as aluminum powder or nickel powder; a conductive whisker such as zinc oxide or potassium titanate; a conductive metal oxide such as titanium oxide; or a conductive polymer such as a polyphenylene derivative. A combination comprising at least two of the foregoing may be used.

The binder is a component that assists in binding of the active material and the conductive agent and binding of the active material to the current collector, and may be added in an amount of about 1 wt % to about 30 wt %, based on the total weight of the mixture including the cathode active material. Examples of the binder may include polyvinylidene fluoride (PVdF), polyvinylidene chloride, polybenzimidazole, polyimide, polyvinyl acetate, polyacrylonitrile, polyvinyl alcohol, carboxymethylcellulose (CMC), starch, hydroxypropylcellulose, regenerated cellulose, polyvinylpyrrolidone, polyethylene, polypropylene, polystyrene, polymethyl methacrylate, polyaniline, acrylonitrile butadiene styrene resin, phenol resin, epoxy resin, polyethylene terephthalate, polytetrafluoroethylene, polyphenylene sulfide, polyamideimide, polyetherimide, polyether sulfone, polyamide, polyacetal, polyphenylene oxide, polybutylene terephthalate, ethylene-propylene-diene terpolymer (EPDM), sulfonated EPDM, styrene butadiene rubber (SBR), fluorine rubber, and various copolymers. A combination of the foregoing may be used.

The filler is a component suppressing the expansion of the cathode, and is selectively used. The filler is not limited as long as it is a fibrous material that does not causing an undesirable chemical change in the battery. Examples of the filler may include an olefin-based polymer, such as polyethylene or polypropylene; and fibrous material, such as glass fiber or a carbon fiber.

The amount of the cathode active material, the amount of the conductive agent, the amount of the filler, the amount of the binder, and the amount of the solvent can be determined by one of skill in the art of the lithium secondary battery without undue experimentation. At least one of the conductive agent, the filler, the binder and the solvent may be omitted depending on the use and configuration of the lithium secondary battery.

For example, N-methylpyrrolidone (NMP) may be used as the solvent, a PVdF or PVdF copolymer may be used as the binder, and carbon black or acetylene black may be used as the conductive agent. For example, 94 wt % of the cathode active material, 3 wt % of the binder, and 3 wt % of the conductive agent are mixed in a powder state, NMP is added such that solid content is 70 wt % to make a slurry, and then this slurry is coated, dried and rolled to prepare a cathode plate.

The cathode current collector is made to have a thickness of about 3 µm to about 50 µm. The cathode current collector is not limited as long as it has high conductivity without causing an undesirable chemical change in the battery. For example, the cathode current collector may include stainless steel, aluminum, nickel, titanium, or carbon, or may include aluminum or stainless steel surface-treated with carbon, nickel, titanium, or silver. The cathode current collector may comprise fine irregularities on its surface, e.g., features having a dimension of about 0.1 micrometer (µm) to 10 µm, to increase the adhesive force of the cathode active material, and may have various forms such as film, sheet, foil, net, porous body, foam, or a nonwoven fabric.

For example, the lithium secondary battery may include a sulfone-containing protective film on the surface of the anode.

As is further described above, the generation of gas at high temperature is caused by the decomposition of the SEI film on the surface of the anode by $Ni^{3+}$ cations eluted from the cathode. Therefore, the lithium secondary battery includes a sulfone-based compound in the electrolyte, and thus a sulfone-containing protective film is formed on the surface of the anode. The protective film may prevent the decomposition of the SEI film to suppress the generation of gas at high temperature.

For example, the anode may include an anode active material including a metal or metalloid alloyable with lithium and/or a carbon-based anode active material.

For example, the anode active material including a metal or metalloid alloyable with lithium may include at least one of silicon (Si), a silicon-carbon (Si—C) composite material including Si particles, or $SiO_{a'}$ (0<a'<2).

For example, the average particle diameter of Si particles in the Si—C composite material may be about 200 nanometers (nm) or less, e.g., about 200 nm to about 10 nm.

For example, the capacity of the Si—C composite material may be about 300 milliampere-hours per gram (mAh/g) to about 700 mAh/g. For example, the capacity of the Si—C composite material may be about 400 mAh/g to about 600 mAh/g.

The anode may include at least one of Sn, Al, Ge, Pb, Bi, Sb, a Si—Y' alloy (Y' is an alkali metal, an alkaline earth metal, a Group 13 element, a Group 14 element, a Group 15 element, a Group 16 element, a transition metal, or a rare earth element, and not Si), or at least one of a Sn—Y' alloy (Y' is an alkali metal, an alkaline earth metal, a Group 13 element, a Group 14 element, a Group 15 element, a Group 16 element, a transition metal, or a rare earth element, and not Sn), in addition to the aforementioned anode active material. The element Y' may be at least one of Mg, Ca, Sr, Ba, Ra, Sc, Y, Ti, Zr, Hf, Rf, V, Nb, Ta, Db, Cr, Mo, W, Sg, Tc, Re, Bh, Fe, Pb, Ru, Os, Hs, Rh, Ir, Pd, Pt, Cu, Ag, Au, Zn, Cd, B, Al, Ga, Sn, In, Tl, Ge, P, As, Sb, Bi, S, Se, Te, or Po.

Next, an anode is prepared by the following method.

The anode may be prepared by applying an anode active material composition onto an anode current collector and drying and pressing the anode active material composition. In addition to the above-described anode active material, an anode active material composition in which a binder and a solvent are mixed is prepared as desired.

A conductive agent, a filler, and the like may be added to the anode active material composition.

Also, the binder, solvent, conductive agent and filler in the anode active material composition may be the same as those in the cathode active material composition.

In the anode active material composition, water may be used as the solvent. For example, water may be used as the solvent, at least one of CMC, SBR, an acrylate polymer or a methacrylate polymer may be used as the binder, and at least one of carbon black, acetylene black, or graphite may be used as the conductive agent. For example, about 94 wt % of the anode active material, about 3 wt % of the binder, and about 3 wt % of the conductive agent are mixed in a powder state, water is added such that solid content is about 70 wt %, based on a total content, to make a slurry, and then this slurry is coated, dried and rolled to prepare an anode plate.

The loading level of the prepared anode active material composition is set depending on the loading level of the cathode active material composition.

The loading level of the anode active material composition may be about 12 milligrams per square centimeter ($mg/cm^2$) or more, for example, about 15 $mg/cm^2$, depending the capacity per gram of the anode active material composition. The electrode density may be 1.5 g/cc or more, for example, 1.6 g/cc or more.

In an embodiment, for high cell energy density, the loading level of the prepared anode active material composition may be about 15 mg/cm² to about 25 mg/cm², and the electrode density may be about 1.6 g/cc to about 2.3 g/cc or more.

When the loading level of the anode active material and the electrode density satisfy the above ranges, a battery including this anode active material may exhibit a high cell energy density of 500 Wh/L or more.

The anode current collector is made to have a thickness of about 3 μm to about 50 μm. This anode current collector is not limited as long as it has high conductivity without causing a chemical change in the battery. For example, the anode current collector may include copper, stainless steel, aluminum, nickel, titanium, or graphitized carbon, may include copper or stainless steel surface-treated with carbon, nickel, titanium or silver, or may include an aluminum-cadmium alloy. Similarly to the cathode current collector, the anode current collector may contain fine irregularities on its surface to increase the adhesive force of the anode active material, and may have various forms such as film, sheet, foil, net, porous body, foam, or a nonwoven fabric.

For example, the operating voltage of the lithium secondary battery may be 2.8 V to 4.3 V.

For example, the cell energy density of the lithium secondary battery may be 500 Wh/L or more.

In an embodiment, the lithium secondary battery may further include a separator between the cathode and the anode. As the separator, an insulating thin film having high ion permeability and mechanical strength may be used. The pore diameter of the separator is about 0.001 μm to about 1 μm, and the thickness thereof is about 3 μm to about 30 μm. As the separator, a sheet or nonwoven fabric, which is made of an olefin-based polymer such as polypropylene having chemical resistance and hydrophobicity, glass fiber, or polyethylene, may be used. When a solid electrolyte such as polymer is used as the electrolyte, the solid electrolyte may serve as the separator.

In addition to the aforementioned electrolyte, a solid electrolyte, an organic solid electrolyte, or an inorganic solid electrolyte may be used.

As the organic solid electrolyte, for example, at least one of a polyethylene derivative, a polyethylene oxide derivative, a polypropylene oxide derivative, a phosphate ester polymer, a polyester sulfide, a polyvinyl alcohol, a polyvinylidene fluoride, or a polymer including an ionic dissociation group may be used.

As the inorganic solid electrolyte, for example, at least one of nitride, halide or sulfate of Li, such as $Li_3N$, LiI, $Li_5NI_2$, $Li_3N$—LiI—LiOH, $Li_2SiS_3$, $Li_4SiO_4$, $Li_4SiO_4$—LiI—LiOH, or $Li_3PO_4$—$Li_2S$—$SiS_2$, may be used.

Figure 1:
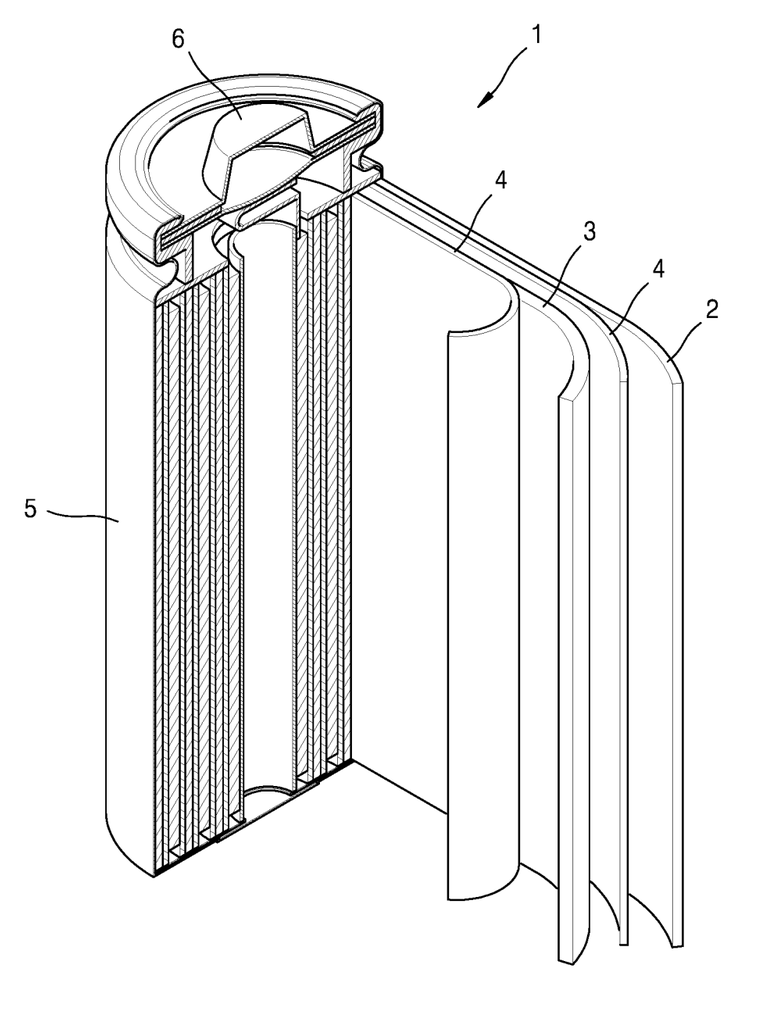

As shown in the FIG. 1, the lithium secondary battery 1 includes a cathode 3, an anode 2, and a separator 4. The cathode 3, the anode 2, and the separator are wound or folded and accommodated in a battery case 5. Then, an electrolyte is injected into the battery case 5, and the battery case 5 is sealed with a cap assembly 6 to complete the lithium secondary battery 1. The battery case 5 may have a cylindrical shape, a rectangular shape, or a thin film shape. For example, the lithium secondary battery 1 may be a large-sized thin-film battery. The lithium secondary battery 1 may be a lithium ion battery.

The electrolyte may be manufactured by contacting a lithium salt, a non-aqueous solvent, a compound represented by Formula 1, and a compound represented by Formula 2 to manufacture the electrolyte:

Formula 1

Formula 2 wherein, in Formulas 1 and 2, $R_1$ to $R_3$ are each independently a substituted or unsubstituted $C_1$-$C_{30}$ alkyl group, a substituted or unsubstituted $C_6$-$C_{60}$ aryl group, or a substituted or unsubstituted $C_1$-$C_{60}$ heteroaryl group, and $R_{11}$ and $R_{12}$ are each independently hydrogen, deuterium, a hydroxyl group, a vinyl group, an allyl group, a substituted or unsubstituted $C_1$-$C_{30}$ alkyl group, a substituted or unsubstituted $C_2$-$C_{10}$ alkenyl group, a substituted or unsubstituted $C_2$-$C_{10}$ alkynyl group, a substituted or unsubstituted $C_6$-$C_{60}$ aryl group, or a substituted or unsubstituted $C_1$-$C_{60}$ heteroaryl group.

The lithium secondary battery may be manufactured by, for example, injecting an electrolyte between the anode and the cathode.

The aforementioned anode, cathode and separator are wound or folded and accommodated in a battery case. Then, an electrolyte is injected into the battery case, and the battery case is sealed with a cap assembly to complete the lithium secondary battery. The battery case may have a cylindrical shape, a rectangular shape, or a thin film shape.

The lithium secondary battery may be a spiral-wound type battery or a prismatic stack type battery according to the shape of an electrode, and may be a cylindrical battery, a rectangular battery, a coin-shaped battery, or a pouch type battery according to the shape and configuration.

Since details of methods of manufacturing these batteries are well known in the art, a detailed description thereof will be omitted for clarity.

According to another aspect, there is provided a battery module including the lithium secondary battery as a unit cell.

According to still another aspect, there is provided a battery pack including the battery module.

According to still another aspect, there is provided a device including the battery pack. Examples of the device may include, but are not limited to, a power tool operated by a power from an electric motor; electric vehicles (EV) including a hybrid electric vehicle (HEV) and a plug-in hybrid electric vehicle (PHEV); an electric motorcycle including an electric bike (E-bike) and an electric scooter (E-scooter); an electric golf cart; or a power storage system.

Further, the lithium secondary battery may be used for other applications that would benefit from high output, high voltage, or high-temperature performance.

Hereinafter, the present disclosure will be described in more detail with reference to Examples and Comparative Examples. However, these Examples are for illustrating the present disclosure, and the scope of the present disclosure is not limited thereto.

EXAMPLES

Example 1

(Preparation of Cathode)

$LiNi_{0.88}Co_{0.08}Mn_{0.04}O_2$ as a cathode active material, carbon black as a conductive agent, and PVdF as a binder were introduced into N-methyl pyrrolidone (NMP) as a solvent at a weight ratio of 94:3:2 to obtain a mixture. The mixture was applied onto both sides of an aluminum foil having a thickness of 16 μm at an application rate of 37 mg/cm$^2$ per side, dried, and then roll-pressed to prepare a cathode having an electrode density of 3.6 g/cc.

(Preparation of Anode)

Graphite, CMC, and SBR were introduced into NMP at a weight ratio of 98:1.5:0.5 to obtain a mixture. The mixture was applied onto both sides of a copper foil having a thickness of 10 μm at an application rate of 21.86 mg/cm$^2$ per side, dried, and then roll-pressed to prepare an anode having an electrode density of 1.65 g/cc.

(Preparation of Electrolyte)

2 vol % of FEC based on the total volume of a non-aqueous solvent, 1 wt % of triethyl phosphite, based on the total weight of an electrolyte, and 0.5 wt % of divinyl sulfone, based on the total weight of an electrolyte were added to 1.15 M $LiPF_6$ and EC/EMC/DMC (volume ratio 2/4/4) to prepare an electrolyte.

(Manufacture of Lithium Secondary Battery)

A separator having a thickness of 16 μm and made of polypropylene was interposed between the cathode and the anode, and the electrolyte is injected to manufacture a lithium secondary battery.

Example 2

A lithium secondary battery was manufactured in the same manner as in Example 1, except that an electrolyte was prepared by adding 1 wt % of allyl phenyl sulfone, based on the total weight of an electrolyte, instead of 0.5 wt % of divinyl sulfone.

Comparative Example 1

A lithium secondary battery was manufactured in the same manner as in Example 1, except that an electrolyte was prepared without adding 1 wt % of triethyl phosphite and 0.5 wt % of divinyl sulfone.

Comparative Example 2

A lithium secondary battery was manufactured in the same manner as in Example 1, except that an electrolyte was prepared without adding 0.5 wt % of divinyl sulfone.

Comparative Example 3

A lithium secondary battery was manufactured in the same manner as in Example 2, except that an electrolyte was prepared without adding 1 wt % of triethyl phosphite.

Comparative Example 4

A lithium secondary battery was manufactured in the same manner as in Example 1, except that $LiNi_{0.6}Co_{0.2}Mn_{0.2}O_2$ was used instead of $LiNi_{0.88}Co_{0.08}Mn_{0.04}O_2$ as a cathode active material.

Comparative Example 5

A lithium secondary battery was manufactured in the same manner as in Example 1, except that 6 wt % of triethyl phosphite was added instead of 1 wt % of triethyl phosphite.

Comparative Example 6

A lithium secondary battery was manufactured in the same manner as in Example 1, except that 4 wt % of divinyl sulfone was added instead of 0.5 wt % of divinyl sulfone.

Comparative Example 7

A lithium secondary battery was manufactured in the same manner as in Example 1, except that 0.05 wt % of triethyl phosphite was added instead of 1 wt % of triethyl phosphite.

Comparative Example 8

A lithium secondary battery was manufactured in the same manner as in Example 1, except that 0.05 wt % of divinyl sulfone was added instead of 0.5 wt % of divinyl sulfone.

Example 3

(Preparation of Cathode)

$LiNi_{0.88}Co_{0.08}Al_{0.04}O_2$ as a cathode active material, carbon black as a conductive agent, and PVdF as a binder were introduced into N-methyl pyrrolidone (NMP) as a solvent at a weight ratio of 94:3:2 to obtain a mixture. The mixture was applied onto both sides of an aluminum foil having a thickness of 16 μm at an application rate of 37 mg/cm$^2$ per side, dried, and then roll-pressed to prepare a cathode having an electrode density of 3.6 g/cc.

(Preparation of Anode)

Graphite, CMC, and SBR were introduced into NMP at a weight ratio of 98:1.5:0.5 to obtain a mixture. The mixture was applied onto both sides of a copper foil having a thickness of 10 μm at an application rate of 21.86 mg/cm$^2$ per side, dried, and then roll-pressed to prepare an anode having an electrode density of 1.65 g/cc.

(Preparation of Electrolyte)

2 vol % of FEC based on the total volume of a non-aqueous solvent, 1 wt % of triethyl phosphite based on the total weight of an electrolyte, and 1 wt % of allyl phenyl sulfone, based on the total weight of an electrolyte were added to 1.15M $LiPF_6$ and EC/EMC/DMC (volume ratio 2/4/4) to prepare an electrolyte.

(Manufacture of Lithium Secondary Battery)

A separator having a thickness of 16 μm and made of polypropylene was interposed between the cathode and the anode, and the electrolyte is injected to manufacture a lithium secondary battery.

Example 4

A lithium secondary battery was manufactured in the same manner as in Example 3, except that an electrolyte was prepared by adding 1 wt % of allyl methyl sulfone, based on the total weight of an electrolyte, instead of 1 wt % of allyl phenyl sulfone.

Example 5

A lithium secondary battery was manufactured in the same manner as in Example 2, except that an electrolyte was prepared by adding 1 wt % of phenyl vinyl sulfone, based on the total weight of an electrolyte, instead of 1 wt % of allyl phenyl sulfone.

Comparative Example 9

A lithium secondary battery was manufactured in the same manner as in Example 3, except that an electrolyte was prepared without adding 1 wt % of allyl phenyl sulfone.

Comparative Example 10

A lithium secondary battery was manufactured in the same manner as in Example 4, except that $LiNi_{0.88}Co_{0.08}Mn_{0.04}O_2$ was used instead of $LiNi_{0.88}Co_{0.08}Al_{0.04}O_2$ as a cathode active material, and an electrolyte was prepared without adding 1 wt % of triethyl phosphite.

Comparative Example 11

A lithium secondary battery was manufactured in the same manner as in Example 3, except that $LiNi_{0.6}Co_{0.2}Al_{0.2}O_2$ was used instead of $LiNi_{0.88}Co_{0.08}Al_{0.04}O_2$ as a cathode active material.

Comparative Example 12

A lithium secondary battery was manufactured in the same manner as in Example 3, except that an electrolyte was prepared by adding 6 wt % of triethyl phosphite, based on the total weight of the electrolyte, instead of 1 wt % of triethyl phosphite.

Comparative Example 13

A lithium secondary battery was manufactured in the same manner as in Example 3, except that an electrolyte was prepared by adding 4 wt % of allyl phenyl sulfone, based on the total weight of the electrolyte, instead of 1 wt % of allyl phenyl sulfone.

Comparative Example 14

A lithium secondary battery was manufactured in the same manner as in Example 3, except that an electrolyte was prepared by adding 0.05 wt % of triethyl phosphite, based on the total weight of the electrolyte, instead of 1 wt % of triethyl phosphite.

Comparative Example 15

A lithium secondary battery was manufactured in the same manner as in Example 3, except that an electrolyte was prepared by adding 0.05 wt % of allyl phenyl sulfone, based on the total weight of the electrolyte, instead of 1 wt % of allyl phenyl sulfone.

Example 6

(Preparation of Cathode)
$LiNi_{0.91}Co_{0.06}Al_{0.03}O_2$ as a cathode active material, carbon black as a conductive agent, and PVdF as a binder were introduced into N-methyl pyrrolidone (NMP) as a solvent at a weight ratio of 94:3:2 and mixed with each other to obtain a mixture. The mixture was applied onto both sides of an aluminum foil having a thickness of 16 μm at an application rate of 37 mg/cm$^2$ per side, dried, and then roll-pressed to prepare a cathode having an electrode density of 3.6 g/cc.

(Preparation of Anode)
SiC (Si-containing anode material having a capacity of 470 mAh/g), CMC, and SBR were introduced into NMP at a weight ratio of 98:1.5:0.5 and mixed with each other to obtain a mixture. The mixture was applied onto both sides of a copper foil having a thickness of 10 μm at an application rate of 21.86 mg/cm$^2$ per side, dried, and then roll-pressed to prepare an anode having an electrode density of 1.65 g/cc.

(Preparation of Electrolyte)
12 vol % of FEC, based on the total volume of a non-aqueous solvent, 1 wt % of $LiPO_2F_2$, 1 wt % of LiBOB, 0.25 wt % of SN, 1 wt % of triethyl phosphite, and 0.5 wt % of divinyl sulfone, based on the total weight of an electrolyte, were added to 1.15M $LiPF_6$ and EC/EMC/DMC (volume ratio 2/4/4) to prepare an electrolyte.

(Manufacture of Lithium Secondary Battery)
A separator having a thickness of 16 μm and made of polypropylene was interposed between the cathode and the anode, and the electrolyte is injected to manufacture a lithium secondary battery.

Example 7

A lithium secondary battery was manufactured in the same manner as in Example 6, except that an electrolyte was prepared by adding 1 wt % of allyl phenyl sulfone, based on the total weight of the electrolyte, instead of 0.5 wt % of divinyl sulfone.

Example 8

A lithium secondary battery was manufactured in the same manner as in Example 6, except that an electrolyte was prepared by adding 1 wt % of allyl methyl sulfone, based on the total weight of the electrolyte, instead of 0.5 wt % of divinyl sulfone.

Comparative Example 16

A lithium secondary battery was manufactured in the same manner as in Example 6, except that an electrolyte was prepared without adding 1 wt % of triethyl phosphite and 0.5 wt % of divinyl sulfone.

Comparative Example 17

A lithium secondary battery was manufactured in the same manner as in Example 7, except that 2 vol % of FEC was used instead of 12 vol % of FEC, and an electrolyte was prepared without adding 1 wt % of $LiPO_2F_2$, 1 wt % of LiBOB, 0.25 wt % of SN, and 1 wt % of triethyl phosphite.

Comparative Example 18

A lithium secondary battery was manufactured in the same manner as in Example 6, except that an electrolyte was prepared without adding 0.5 wt % of divinyl sulfone.

Evaluation Example 1: Evaluation of Resistance Increase Rate and Gas Reduction Characteristics The lithium secondary batteries manufactured in Examples 1 to 8 and Comparative Examples 1 to 18 were stored at 60° C. for 10 days, and the resistance increase and initial gas generation amounts were measured. The lithium secondary batteries were then charged and discharged for 200 cycles at 45° C. using a constant current-constant voltage (CCCV) regime under conditions of a charge-discharge current of 1 C/1 C for the constant current portion between 2.8V and 4.25 V, and a cut-off of ⅒ C for the constant voltage portion, and then final gas generation amounts for each of the batteries were measured. The measured results are given in Table 1. The resistance increase was determined by calculating a ratio of resistance after storing at 60° C. for 10 days based on the initial resistance of the lithium secondary battery. A C rate means a current which will discharge a battery in one hour, e.g., a C rate for a battery having a discharge capacity of 1.6 ampere-hours would be 1.6 amperes.

TABLE 1

|  | Resistance increase (%) | Initial gas generation amount (mL/g) | Final gas generation amount (mL/g) |
| --- | --- | --- | --- |
| Example 1 | 108 | 0.21 | 0.40 |
| Example 2 | 108 | 0.26 | 0.42 |
| Comparative Example 1 | 107 | 0.35 | 0.50 |
| Comparative Example 2 | 107 | 0.31 | 0.52 |
| Comparative Example 3 | 109 | 0.39 | 0.51 |
| Comparative Example 4 | 115 | 0.25 | not measured |
| Comparative Example 5 | 104 | 0.56 | not measured |
| Comparative Example 6 | 106 | 0.23 | not measured |
| Comparative Example 7 | 116 | 0.31 | 0.21 |
| Comparative Example 8 | 108 | 0.55 | 0.51 |
| Example 3 | 108 | 0.21 | 0.32 |
| Example 4 | 105 | 0.21 | not measured |
| Example 5 | 108 | 0.22 | not measured |
| Comparative Example 9 | 107 | 0.34 | not measured |
| Comparative Example 10 | 113 | 0.36 | not measured |
| Comparative Example 11 | 116 | 0.26 | not measured |
| Comparative Example 12 | 107 | 0.51 | not measured |
| Comparative Example 13 | 105 | 0.23 | not measured |
| Comparative Example 14 | 117 | 0.35 | 0.28 |
| Comparative Example 15 | 106 | 0.49 | 0.45 |
| Example 6 | 104 | 0.28 | not measured |
| Example 7 | 106 | 0.29 | not measured |
| Example 8 | 105 | 0.29 | not measured |
| Comparative Example 16 | 112 | 0.42 | not measured |
| Comparative Example 17 | 109 | 0.44 | not measured |
| Comparative Example 18 | 116 | 0.39 | not measured |

Evaluation Example 2: Evaluation of Initial Resistance and Lifetime Retention Rate The initial resistance of each of the lithium secondary batteries manufactured in Examples 1 to 3 and 5 and Comparative Examples 1, 4, 5, 6, and 11 to 13 at 60° C. were measured. The lithium secondary batteries were then charged and discharged for 200 cycles at 45° C. using a constant current-constant voltage (CCCV) regime under conditions of a charge-discharge current of 1 C/1 C, for the constant current portion between 2.8 V and 4.25 V, and a cut-off of ⅒ C for the constant voltage portion, and then capacity retention were measured. The measured results are given in Table 2.

TABLE 2

|  | Initial resistance (milliohms, mΩ) | Capacity retention (%) |
| --- | --- | --- |
| Example 1 | 132 | 84.2 |
| Example 2 | 145 | 83.1 |

TABLE 2-continued

|  | Initial resistance (milliohms, mΩ) | Capacity retention (%) |
| --- | --- | --- |
| Comparative Example 1 | 125 | 84.3 |
| Comparative Example 4 | 151 | 75.3 |
| Comparative Example 5 | 131 | 80.1 |
| Comparative Example 6 | 202 | 56.6 |
| Example 3 | 126 | 85.2 |
| Example 5 | 131 | 83.2 |
| Comparative Example 11 | 134 | 74.5 |
| Comparative Example 12 | 145 | 81.2 |
| Comparative Example 13 | 176 | 62.4 |

As indicated in Table 1, the lithium secondary batteries of Examples 1 to 8, each with an electrolyte that includes both a phosphite-based compound and a sulfone-based compound, had excellent gas reduction characteristics while exhibiting excellent resistance increase inhibition characteristics or a predetermined level of resistance increase inhibition characteristics, as compared with the lithium secondary batteries of Comparative Examples 1 and 16, each of which included an electrolyte with no phosphite-based compound and sulfone-based compound, and lithium secondary batteries of Comparative Examples 2, 3, 9, 10, 17, and 18, each of which included an electrolyte with only one of the two, i.e., either the phosphite-based compound or the sulfone-based compound.

In addition, as shown in Tables 1 and 2, in the case of the lithium secondary batteries of Comparative Examples 4 and 11, each using a low-Ni-content cathode, a resistance increased, and a capacity retention decreased, as compared with the lithium secondary batteries of Examples 1 to 8. Further, in the case of the lithium secondary batteries of Comparative Examples 5 and 12, each of which included an excess amount of a phosphite-based compound, exhibited not as good a resistance increase, and the gas generation amount increased, as compared with the lithium secondary batteries of Examples 1 to 8. While not wanting to be bound by theory, these results suggest that an excess amount of the phosphite-based compound decomposes at the anode.

Further, the lithium secondary batteries of Comparative Examples 6 and 13, each including an excess amount of a sulfone-based compound, were not bad in resistance increase and gas generation inhibition, and the initial resistance was large, and a capacity retention rapidly decreased, as compared with the lithium secondary batteries of Examples 1 to 8. These results suggest that an excess amount of the sulfone-based compound forms a high-resistance SEI.

Further, as compared with the lithium secondary batteries of Examples 1 to 8, in the case of the lithium secondary batteries of Comparative Examples 7, 8, 14 and 15, each including a small amount of an additive, a resistance increase was large when the amount of the phosphite-compound is small, and gas generation increased with smaller amounts of the sulfone-based compound. These results suggest that the phosphite-based compound suppresses the resistance increase of the cathode and the sulfone-based compound suppresses the gas generation from the anode.

According to an embodiment, as the amount of nickel in the cathode active material increases the capacity of the lithium secondary battery is maximized. Further, if the electrolyte includes a select amount of a phosphite-based compound and a select amount of a sulfone-based compound, the lithium secondary battery exhibits effects of suppressing a resistance increase, suppressing lifetime deterioration, and reducing gas.

It should be understood that embodiments described herein should be considered in a descriptive sense only and not for purposes of limitation. Descriptions of features or aspects within each embodiment should be considered as available for other similar features or aspects in other embodiments.

While an embodiment has been described with reference to the figures, it will be understood by those of ordinary skill in the art that various changes in form and details may be made therein without departing from the spirit and scope as defined by the following claims.

What is claimed is:

1. An electrolyte comprising:
   a lithium salt;
   a non-aqueous solvent;
   a compound represented by Formula 1; and
   a compound represented by Formula 2

Formula 1

Formula 2 wherein, in Formulas 1 and 2,
$R_1$ to $R_3$ are each independently a substituted or unsubstituted $C_1$-$C_{30}$ alkyl group, a substituted or unsubstituted $C_6$-$C_{60}$ aryl group, or a substituted or unsubstituted $C_1$-$C_{60}$ heteroaryl group, and
$R_{11}$ and $R_{12}$ are each independently hydrogen, deuterium, a hydroxyl group, a vinyl group, an allyl group, a substituted or unsubstituted $C_1$-$C_{30}$ alkyl group, a substituted or unsubstituted $C_2$-$C_{10}$ alkenyl group, a substituted or unsubstituted $C_2$-$C_{10}$ alkynyl group, a substituted or unsubstituted $C_6$-$C_{60}$ aryl group, or a substituted or unsubstituted $C_1$-$C_{60}$ heteroaryl group.

2. The electrolyte of claim 1, wherein the compound of Formula 1 is present in an amount of about 0.1 weight percent to about 5 weight percent, based on a total weight of the electrolyte.

3. The electrolyte of claim 1, wherein the compound of Formula 2 is present in an amount of about 0.1 weight percent to about 3 weight percent, based on a total weight of the electrolyte.

4. The electrolyte of claim 1, wherein $R_1$ to $R_3$ are each independently a methyl group, an ethyl group, a propyl group, an isopropyl group, a butyl group, a sec-butyl group, a tert-butyl group, an isobutyl group, or a phenyl group, each of which is optionally substituted with at least one of deuterium, —F, —Cl, —Br, —I, a cyano group, a nitro group, a hydroxyl group, a methyl group, an ethyl group, or a propyl group.

5. The electrolyte of claim 1, wherein the compound of Formula 1 is at least one of trimethyl phosphite, triethyl phosphite, tributyl phosphite, triphenyl phosphite, tri-o-tolyl phosphite, tri(2-furyl) phosphite, or diethyl phenyl phosphite.

6. The electrolyte of claim 1, wherein at least one of $R_{11}$ or $R_{12}$ is a vinyl group or an allyl group.

7. The electrolyte of claim 1, wherein the compound of Formula 2 is at least one of Compounds 101, 102, 103, 104, or 105

8. The electrolyte of claim 1, wherein the lithium salt is at least one of lithium difluoro (oxalate)borate, lithium bis(oxalato)borate, lithium difluoro bis(oxalato) phosphate, $LiPO_2F_2$, $LiBF_4$, $LiPF_6$, $LiCF_3SO_3$, $LiN(CF_3SO_2)_2$, or $LiN(FSO_2)_2$.

9. The electrolyte of claim 1, wherein the non-aqueous solvent is at least one of dimethyl carbonate, diethyl carbonate, ethyl methyl carbonate, dipropyl carbonate, methyl propyl carbonate, ethyl propyl carbonate, ethylene carbonate, propylene carbonate, or butylene carbonate.

10. The electrolyte of claim 1, wherein the non-aqueous solvent includes fluoroethylene carbonate.

11. The electrolyte of claim 1, further comprising at least one of vinylene carbonate, vinylethylene carbonate, maleic anhydride, succinic anhydride, or succinonitrile.

12. A lithium secondary battery comprising:
    a cathode;
    an anode; and
    the electrolyte of claim 1 disposed between the cathode and the anode,
    wherein the cathode includes a cathode active material represented by Formula 3, $$Li_xNi_yM_{1-y}O_{2-z}A_z,$$ Formula 3 wherein, in Formula 3,
0.9≤x≤1.2, 0.1≤y≤0.98, and 0≤z<0.2,
M is at least one of Al, Mg, Mn, Co, Fe, Cr, V, Ti, Cu, B, Ca, Zn, Zr, Nb, Mo, Sr, Sb, W, or Bi, and
A is an element having an oxidation number of −1, −2, or −3.

13. The lithium secondary battery of claim 12, wherein, in Formula 3, 0.8≤y≤0.98.

14. The lithium secondary battery of claim 12, wherein the cathode active material is represented by Formulae 4 or 5:

$$Li_{x'}Ni_{y'}Co_{1-y'-z'}Al_{z'}O_2, \text{ or} \qquad \text{Formula 4}$$

$$Li_{x'}Ni_{y'}Co_{1-y'-z'}Mn_{z'}O_2, \qquad \text{Formula 5}$$

wherein for the cathode active materials of Formulae 4 or 5, x', y', and z' are each independently 0.9≤x'≤1.2, 0.8≤y'≤0.98, 0<z'<0.1, and 0<1−y'−z'<0.2.

15. The lithium secondary battery of claim 12, wherein the cathode active material is at least one of $LiNi_{0.88}Co_{0.08}Mn_{0.04}O_2$, $LiNi_{0.88}Co_{0.08}Al_{0.04}O_2$, $LiNi_{0.91}Co_{0.06}Mn_{0.03}O_2$, $LiNi_{0.91}Co_{0.06}Al_{0.03}O_2$, $Li_{1.02}Ni_{0.88}Co_{0.08}Mn_{0.04}O_2$, $Li_{1.02}Ni_{0.88}Co_{0.08}Al_{0.04}O_2$, $Li_{1.02}Ni_{0.91}Co_{0.06}Mn_{0.03}O_2$, or $Li_{1.02}Ni_{0.91}Co_{0.06}Al_{0.03}O_2$.

16. The lithium secondary battery of claim 12, wherein the cathode has a BET specific surface area of about 8 square meters per gram to about 10 square meters per gram, and a tap density of about 3 grams per cubic centimeter or more.

17. The lithium secondary battery of claim 12, further comprising a sulfone-containing protective film on a surface of the anode.

18. The lithium secondary battery of claim 12, wherein the anode includes an anode active material comprising at least one of a metal alloyable with lithium, a metalloid alloyable with lithium, or a carbonaceous anode active material.

19. The lithium secondary battery of claim 18, wherein the metalloid alloyable with lithium is at least one of silicon, a silicon-carbon composite material comprising a Si particle, or a silicon oxide of the formula $SiO_{a'}$, wherein 0<a'<2.

20. The lithium secondary battery of claim 12, wherein the lithium secondary battery has a cell energy density of 500 Watt-hours per liter or greater.

* * * * *